(12) United States Patent
Tanner et al.

(10) Patent No.: US 7,585,357 B2
(45) Date of Patent: Sep. 8, 2009

(54) MULTIPLE USE SEPTUM FOR INJECTION PORTS FOR GAS CHROMATOGRAPHY OR THE LIKE

(75) Inventors: Douglas E. Tanner, Germantown, NY (US); Craig Busby, Sherman, CT (US); Albert J. Corey, Poughkeepsie, NY (US)

(73) Assignee: Pawling Corporation, Pawling, NY (US)

( * ) Notice: Subject to any disclaimer, the term of this patent is extended or adjusted under 35 U.S.C. 154(b) by 349 days.

(21) Appl. No.: 11/693,250

(22) Filed: Mar. 30, 2007

(65) Prior Publication Data

US 2008/0236395 A1    Oct. 2, 2008

(51) Int. Cl.
G01N 1/00    (2006.01)

(52) U.S. Cl. .............................. 96/105; 95/89; 73/23.41

(58) Field of Classification Search ............. 95/82, 95/89; 96/101, 105; 73/23.35, 23.41
See application file for complete search history.

(56) References Cited

U.S. PATENT DOCUMENTS

| | | | | |
|---|---|---|---|---|
| 4,084,718 A * | 4/1978 | Wadsworth | | 215/247 |
| 4,422,860 A * | 12/1983 | Feinstein | | 95/87 |
| 4,954,149 A | 9/1990 | Fullemann | | |
| 5,012,845 A | 5/1991 | Averette | | |
| 5,062,310 A | 11/1991 | Eaton | | |
| 5,252,109 A * | 10/1993 | Munari et al. | | 95/87 |
| 5,400,666 A * | 3/1995 | Song | | 73/864.21 |
| 5,531,810 A * | 7/1996 | Fullemann | | 96/105 |
| 5,707,589 A | 1/1998 | Fullemann | | |
| 5,714,677 A * | 2/1998 | Parsy et al. | | 73/23.41 |
| 5,929,321 A * | 7/1999 | Bertrand | | 73/23.39 |
| 6,093,371 A * | 7/2000 | Wilson | | 422/89 |
| 6,484,560 B1 * | 11/2002 | Prest | | 73/23.41 |
| 6,652,625 B1 * | 11/2003 | Tipler et al. | | 95/82 |
| 7,105,043 B2 * | 9/2006 | O'Neil | | 96/101 |
| 7,517,395 B2 * | 4/2009 | Logan | | 96/105 |
| 2005/0256500 A1 | 11/2005 | Fujii | | |
| 2008/0282814 A1 * | 11/2008 | Coleman et al. | | 73/863.71 |

OTHER PUBLICATIONS

"Separation Times", pp. 6 and 7, vol. 15, No. 2, 2002, www.agilent.com/chem.

* cited by examiner

Primary Examiner—Duane Smith
Assistant Examiner—Robert A Clemente
(74) Attorney, Agent, or Firm—St. Onge Steward Johnston & Reens LLC

(57) ABSTRACT

A new septum for multiple use injection ports enabling the introduction of fluid materials by needle injection into a gas chromatograph or other system under positive pressure. The injection port utilizes a special septum to seal the port while accommodating passage of an injection needle. The septum is provided with an axial through passage, preferably of greater diameter than the injection needle. The septum, which is formed of elastomeric material, is placed under axial compression sufficient to inwardly displace the material surrounding the preformed opening, to tightly close and seal the opening against the pressure of the system. The septum may be penetrated multiple times by injection needles without coring or otherwise damaging the septum. Greater operating life is achieved and contamination of the system is minimized.

9 Claims, 2 Drawing Sheets

MULTIPLE USE SEPTUM FOR INJECTION PORTS FOR GAS CHROMATOGRAPHY OR THE LIKE

BACKGROUND OF THE INVENTION

In gas chromatography, a liquid sample is injected into a gaseous system, maintained under elevated pressure (e.g. 20 psi), where it undergoes analysis in accordance with well known procedures. To simplify injection of the sample material into the pressurized system, the equipment is provided with injection ports sealed by an elastomeric septum. Injection needles are utilized to penetrate the septum and to inject the sample material into the pressurized ambient, after which the needles are withdrawn and the system is automatically resealed by nature of the elastomeric septum's self-sealing properties.

In practice, the injection ports are penetrated multiple times by injection needles over the course of time, until the septum becomes degraded by tearing and coring, which causes the system to not function properly. At this stage, the septum must be replaced, requiring the instrument to be temporarily taken out of service.

With known systems, multiple penetration of a septum typically causes it to become torn and ragged in the penetrated area, and in many instances to be cored by the injection needle. When this occurs, small bits of the septum material can enter the pressurized gas stream of the chromatograph. The chromatograph then senses the presence of the foreign material and delivers a read-out that is at least partially in error as a function of sensing the foreign material along with the material of the test specimen.

SUMMARY OF THE INVENTION

In accordance with the present invention, a new and improved septum is provided for injection ports which enable greatly extended usage of the septum for multiple use injections and which virtually eliminates the problem of poor reading due to tearing and coring of the septum material. To this end, the present invention provides a novel and improved form of elastomeric septum, which is provided with an axial through passage, preferably of a diameter greater than the expected injection needle. The septum typically is in the form of a flat washer. When placed in the injection port, it is confined peripherally, and placed under axial compression between a pedestal and a removable cap. The removable cap, which is provided with an entrance opening for the injection needle, is threadedly secured to the pedestal and is tightened on to the pedestal to compress the septum sufficiently to close the through opening thereof tightly and form a tight seal against the internal pressure of the chromatograph or other system.

When an injection needle is applied to the injection port, it penetrates the septum at the position of the opening therein. Advantageously, the injection needle is typically a blunt-ended needle, which simply displaces the material of the septum that surrounds and defines the through opening. Thus, the septum is neither cut nor cored during the penetration of the injection needle.

With the injection port septum of the invention, not only is the working lifetime of the septum greatly increased, but throughout its working life the septum remains substantially free of the kind of coring and tearing that is typical of conventional septa, such that more precise test results can be derived, and more efficient use of the expensive test systems may be realized.

For a more complete understanding of the above and other features and advantages of the invention, reference should be made to the following detailed description of a preferred embodiment, and to the accompanying drawings.

DESCRIPTION OF A PREFERRED EMBODIMENT

Figure 3:
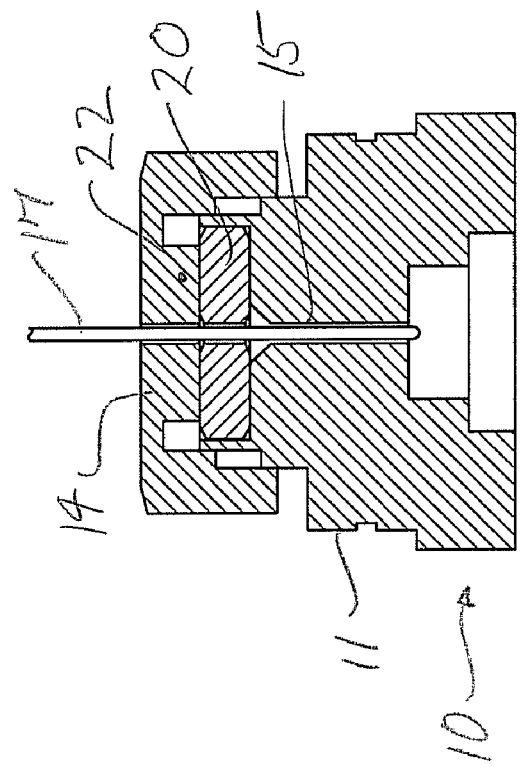
FIG. 3 is a cross sectional view similar to FIG. 2 showing the septum in a compressed and sealed condition.
Figure 4:
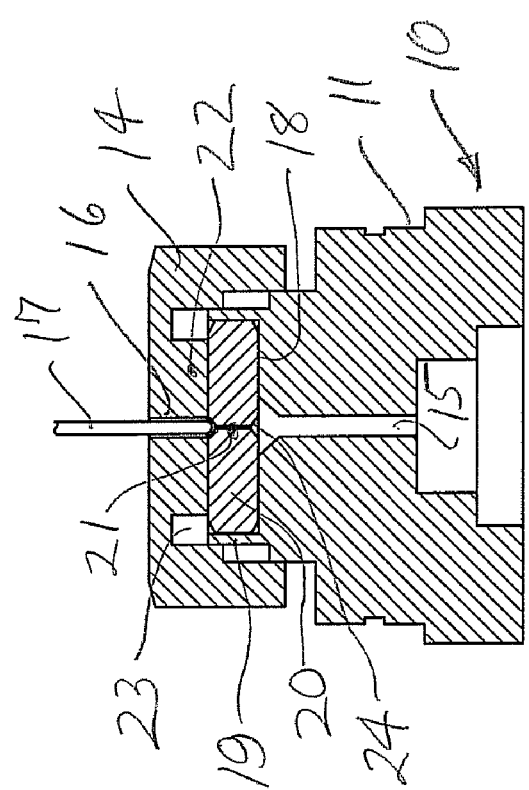
FIG. 4 is a cross sectional view similar to FIG. 3, but showing an injection needle penetrating the septum and in position to eject sample material into the sealed, pressurized system.

Referring now to the drawings, the reference numeral 10 designates generally a typical injection port of a type suitable for incorporation in a pressurized system, such as a gas chromatograph (not shown). The injection port 10 includes a pedestal 11, the upper portion of which is threaded at 12 for engagement with corresponding threads 13 of a cap 14. Both the pedestal 11 and the cap 14 are formed with injection passages 15, 16, which are axially aligned and arranged to receive injection needles 17 (FIGS. 3, 4). For a typical gas chromatograph system, the injection needle 17 may have a diameter $D_1$ of approximately 0.025 inch.

In the illustrated arrangement, the pedestal 11 includes a flat, upwardly facing seat 18 surrounded by a circular collar 19 which projects upwardly a short distance from the level of the seat. The collar 19 is annular in form and its outer surfaces carry the pedestal threads 12.

Figure 2:
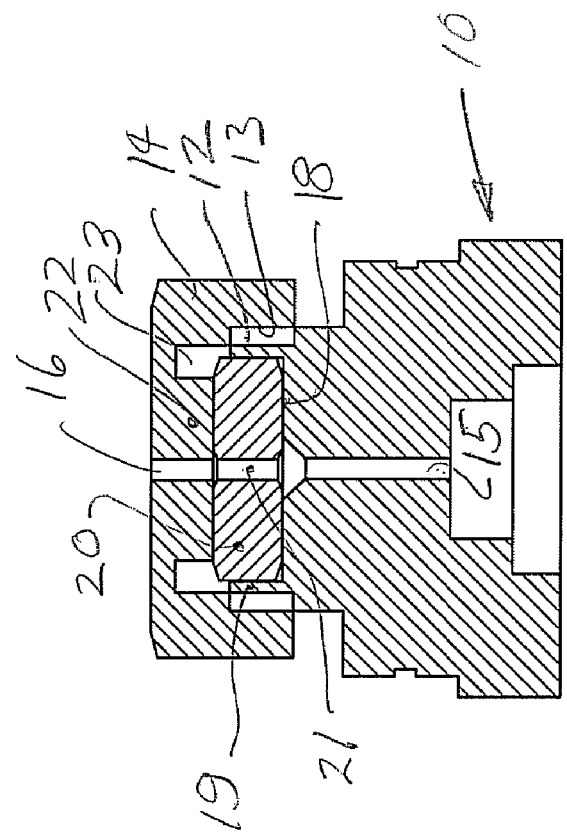
FIG. 2 is a cross sectional view as taken generally on line 2-2 of FIG. 1, illustrating the new septum installed in the injection port but not yet compressed.
Figure 1:
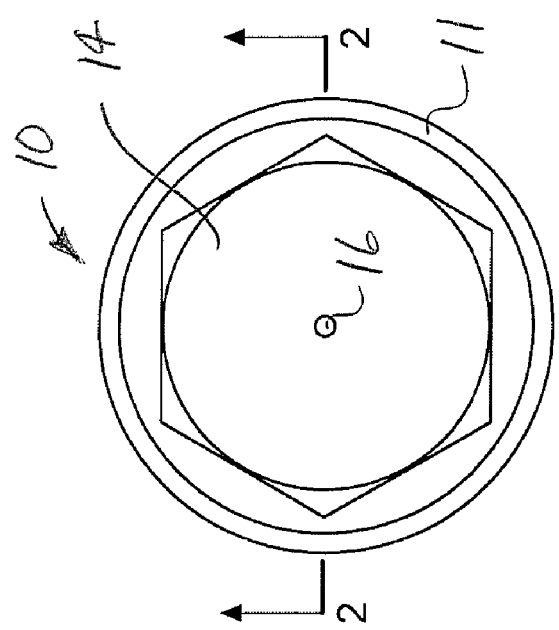
FIG. 1 is a top plan view of an injection port for a gas chromatograph or the like incorporating a septum according to the invention.

A circular septum 20 is positioned on the seat 18, closely surrounded by the annular collar 19, substantially as shown in FIG. 2. The septum 20 is formed of an elastomeric material, such as silicone rubber. Pursuant to the invention, the septum is provided with a central axial through opening 21 which is aligned with the injection passages 15, 16 in the pedestal and cap respectively. In the illustrated form of the invention, the injection passages 15, 16 are formed with diameters which are at least slightly greater than the diameter of the injection needle 17. The through opening 21 of the septum 20 preferably is of a diameter which is somewhat larger than the diameter of the needle 17. In this respect, we have found that a diameter of 0.040 inch for the passage 21 is suitable when using an injection needle having a diameter of 0.025 inch.

In accordance with the invention, when the septum 20 is installed on the pedestal (see 18) as shown in FIG. 2, it is peripherally confined by the collar 19 and is axially aligned with the injection passages. In a typical (but non-limiting) embodiment, a septum 20 according to the invention may be in the form of a washer, with a diameter of about 0.420 inch and an initial thickness of about 0.130 inch. It will be understood, however, that injection ports provided by different manufacturers may have different dimensions, and septa according to the invention may be sized appropriately for use with the various port configurations.

When the cap 14 is rotated and tightened down, by action of the threads 12, 13, a downwardly facing compression boss 22, located on the underside of the cap 14 and surrounded by a recess 23, engages the upper surface of the septum and compresses it axially against the pedestal seat 18. Inasmuch as the septum is confined peripherally by the collar 19, the axial compression of the septum causes the material surrounding the through opening 21 to be displaced radially inward, as reflected in FIG. 3. After a predetermined amount of tightening of the cap 14, the septum through passage 21 is tightly closed and sealed, so as to prevent leakage of gas from the pressurized system.

In the typical example illustrated, the septum may be compressed axially in amount greater than about 20% of its initial thickness. Thus, a septum 20 with an initial thickness of about 0.130 may be compressed to a thickness of about 0.100. This will achieve a full closure and tight sealing of the through passage 21. Particular combinations of septa and port hardware may require or permit greater or lesser compression to achieve a tight closure of the septum passage.

To inject a test sample into the injection port 10, the injection needle 17 is forced through the closed passage 21 of the septum, entering and passing through the injection passage 16 as shown in FIG. 4. After the injection has been performed, the needle 17 is withdrawn, and the septum passage 21 returns to its tightly closed and sealed condition, as shown in FIG. 3.

After the septum has been compressed by tightening of the cap 14, and the septum passage 21 has become tightly closed and sealed, slight "dimpled" areas remain at the top and bottom of the passage 21, as reflected at 24 in FIG. 3. This helps to guide the injection needle into the passage 21 as the needle first comes into contact with upper portions of the septum. It will be understood, in this respect, that the injection needle 17 will be rather accurately guided toward the septum passage 21 by means of the injection passage 16 provided in the cap 14. Nevertheless, the dimples 24 assist in starting the injection needle into the otherwise tightly closed passage.

Because the septum of the invention is not subject to the tearing and coring that is characteristic of conventional septa, the new septum usually can be retained in service for a thousand or more injections before replacement may be indicated. The extended operating life of the new septa is significant, in that it allows the costly gas chromatograph or other equipment to be maintained in continued operation over a much longer period of time without contaminating the system with small pieces of torn or cored septa material, which can lead to false or inaccurate test results. The new injection port also results in more effective and efficient use of the expensive equipment.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

The invention claimed is:

1. A multiple use injection port for the introduction of fluid materials by needle injection into a system under positive pressure, and of the type which comprises
   (a) an injection pedestal having a central axis and having an upwardly facing generally flat compression seat disposed on said axis for the support of a sealing septum,
   (b) said injection pedestal having an injection passage extending axially from said seat to provide communication with said system under positive pressure,
   (c) said injection passage being of a diameter to accommodate the insertion of an injection needle,
   (d) a sealing septum, formed of resilient, elastomeric material, supported on said seat,
   (e) an injection port cap threadedly engaging said pedestal and positioned over the top of said septum,
   (f) said cap having an axial guide opening aligned with said injection passage and being of a diameter to accommodate the passage of an injection needle,
   (g) said cap having a generally flat compression surface positioned above the upper surface of said septum and said seat and arranged to axially compress said septum against said seat when said cap is tightened onto said pedestal, characterized by
   (h) said septum being of flat form and having generally flat upper and lower surfaces defining a thickness, and having a transverse dimension substantially greater than said thickness,
   (i) said septum being initially formed with an axial through opening extending throughout the thickness of the septum and which, when the septum is supported on said seat, is aligned with the injection passage and guide opening,
   (j) said compression seat and said compression surface serving to act upon the upper and lower surfaces of said septum to axially compress said septum in the thickness direction such that the septum material surrounding the through passage in said septum is displaced in a radially inward direction sufficiently to fully close the septum's through passage and form a seal against the positive pressure of said system, and
   (k) the material surrounding said fully closed axial through opening being subject to radially outward displacement while said septum remains under axial compression to accommodate the axial passage of an injection needle through the septum passage and into the injection passage in said pedestal.

2. The multiple use injection port of claim 1, wherein
   (a) the through passage in said septum, prior to compression thereof, has an initial diameter which is equal to or greater than the diameter of said injection needle.

3. The multiple use injection port of claim 2, wherein
   (a) the initial diameter of the septum through passage is approximately 0.040 inch for a needle having a diameter of approximately 0.025 inch.

4. The multiple use injection port of claim 1, wherein
   (a) said septum is in the form of a generally flat circular washer.

5. The multiple use injection port of claim 4, wherein
   (a) said septum has an initial thickness and is compressed axially in an amount greater than 20% of its initial thickness when said injection port cap is tightened onto said pedestal.

6. The multiple use injection port of claim 5, wherein
   (a) said septum has an initial diameter of about 0.420 inch and an initial thickness of about 0.130 inch, and
   (b) said septum has a compressed thickness of about 0.100 inch.

7. The multiple use injection port of claim 1, wherein
   (a) one of said pedestal and cap forms a collar surrounding said seat for the lateral confinement and positioning of said septum during axial compression thereof.

8. A septum adapted specially for use in a gas chromatograph injection port or the like, the septum being of a flat circular form of having a substantially greater diameter than thickness and being formed of elastomeric material, said septum being initially formed with a central axial through opening extending throughout the thickness of said septum, said septum, when subjected to axial compression, being reformed by radially inward displacement of material thereof surrounding said through opening to effect tight closure of said axial through opening, the material of said septum immediately surrounding and defining said axial through opening being radially outwardly displaceable while said septum remains under said axial compression to accommodate axial insertion of an injection needle through the septum.

9. A septum according to claim 8, in which said axial through opening, prior to axial compression of said septum, has a diameter greater than a diameter of said injection needle.

* * * * *